United States Patent [19]

Linhardt et al.

[11] Patent Number: 5,284,558
[45] Date of Patent: Feb. 8, 1994

[54] ELECTROPHORESIS-BASED SEQUENCING OF OLIGOSACCHARIDES

[75] Inventors: Robert J. Linhardt; Kyung-Bok Lee; Ali Al-Hakim, all of Iowa City, Iowa; Duraikkannu Loganathan, Ann Anbor, Mich.

[73] Assignee: University of Iowa Research Foundation, Iowa City, Iowa

[21] Appl. No.: 558,708

[22] Filed: Jul. 27, 1990

[51] Int. Cl.$^5$ .................. G01N 27/447; G01N 27/26; G01N 33/48; C12Q 1/34
[52] U.S. Cl. .................. 204/182.8; 435/18; 435/212; 436/94; 536/127; 536/18.5
[58] Field of Search .................. 435/274, 18, 212; 436/94; 204/182.8, 182.9, 180.1, 299 R

[56] References Cited

U.S. PATENT DOCUMENTS

| | | | |
|---|---|---|---|
| 4,751,084 | 6/1988 | Feder | 435/212 |
| 4,851,517 | 7/1989 | Feder | 536/1.1 |
| 4,975,165 | 12/1990 | Brandley et al. | 204/182.1 |
| 5,019,231 | 5/1991 | Brandley | 204/182.1 |
| 5,035,786 | 7/1991 | Brandley et al. | 204/182.1 |
| 5,100,778 | 3/1992 | Rademacher et al. | 435/22 X |
| 5,104,508 | 4/1992 | Williams et al. | 204/182.8 |

FOREIGN PATENT DOCUMENTS

WO88/10422 12/1988 PCT Int'l Appl.

OTHER PUBLICATIONS

Lee et al., *Appl. Biochem. and Biotechnol.*, 23:53-80 (1990).
Al-Hakim et al., *Electrophoresis*, 11:23-28 (1990).
Rice et al., *Biochem. J.*, 244:515-522 (1987).
Oku et al., *Anal. Biochem.*, 185:331-334 (1990).
Takara Advertising Literature.
Welply, *TIBTECH*, 7:5-10 (1989).
Koller et al., *Chemical Abstracts*, 111:649, Abstract 32889y (1989).

*Primary Examiner*—John Niebling
*Assistant Examiner*—John S. Starsiak, Jr.
*Attorney, Agent, or Firm*—Hamilton, Brook, Smith & Reynolds

[57] ABSTRACT

The electrophoretic isolation and monosaccharide sequence determination of a neutral or weakly acidic oligosaccharide species of interest are disclosed. A labeling compound and a charged group are coupled to the reducing end of the species of interest, thereby facilitating electrophoretic separation and detection of the separated species. The resolved species of interest can then be recovered from the electrophoretic medium, for example, by electrophoretic transfer to a charged solid support.

Following isolation, monosaccharide units can be cleaved successively from the non-reducing end of the species of interest to reveal the monosaccharide sequence. The identity of each monosaccharide unit is determined by correlating cleavage data with known exoglycosidase specificites.

19 Claims, 5 Drawing Sheets

Scheme. R=H, β-D-Gal-(1→4)-, or β-D-Gal-(1→4)-β-D-Gal-(1→4)-

Scheme. R=H, β-D-Gal-(1→4)-, or β-D-Gal-(1→4)-β-D-Gal-(1→4)-

ELECTROPHORESIS-BASED SEQUENCING OF OLIGOSACCHARIDES

BACKGROUND OF THE INVENTION

The simple sugars are among the most important small organic molecules in the cell. The simplest type of sugars, the monosaccharides, are compounds having the general formula $(CH_2O)_n$, where n is an integer from three through seven. All sugars contain hydroxyl groups and either an aldehyde or a ketone group. Sugar monomers can be combined via a glycosidic bond by the reaction of a hydroxyl group of one sugar with the aldehyde or ketone group of a second sugar to form disaccharides, oligosaccharides and polysaccharides. Because each monosaccharide has several reactive hydroxyl groups, complex sugars can exhibit branching rather than a simple linear architecture.

Simple polysaccharides such as glycogen, which exhibits a repeating structure of glucose monomers, are used principally as energy stores by the cell. Smaller, but more complex oligosaccharides function in other important cellular roles. For example, such oligosaccharides can be linked to proteins or lipids to form glycoproteins or glycolipids, respectively.

In recent years, a major focus for researchers in the area of carbohydrate chemistry has been the glycoproteins. The oligosaccharide side chains of glycoproteins have been implicated in such cellular processes as protection of peptide chains against proteolytic attack, facilitation of the secretion of certain proteins or their mobilization to the cell surface, induction and maintainance of the protein conformation in a biologically-active form, clearance of glycoproteins from plasma, direction of the immune response by acting as immune decays, and function as antigenic determinants in differentiation and development.

Information about glycoprotein sugar side-chain composition, and more importantly their sequence is required to fully understand and establish structure-function relationships. However, glycoproteins are usually available in only limited quantities (typically 1-100 micrograms glycoprotein, containing 1-10% oligosaccharide) making it difficult to determine the sequence and anomeric configuration of glycosidic linkage. Unfortunately, current techniques employed to determine oligosaccharide sequence require milligram quantities of the oligosaccharide species. A need exists for a simplified oligosaccharide sequencing method which is useful to determine the sequence when only small (e.g., microgram quantities) quantities of common oligosaccharides are available.

SUMMARY OF THE INVENTION

This invention pertains to methods for the isolation and purification of a neutral or weakly acidic oligosaccharide species of interest from a mixture of oligosaccharide components. A labeling compound and a charged group are coupled to the reducing end of the oligosaccharide components in the mixture to produce a derivatized species of interest. The oligosaccharide components are resolved in a electrophoretic medium and the derivatized species of interest is then recovered from the electrophoretic medium, for example, by electrophoretic transfer to a charged solid support.

In another aspect, the invention pertains to methods for determining the monosaccharide sequence of a neutral or weakly acidic oligosaccharide species of interest having size X. As used herein, the variable X represents the number of monosaccharide units in the oligosaccharide species of interest. A labeling compound and a charged group are coupled to the reducing end of the oligosaccharide species of interest to produce a derivatized species of interest.

Individual samples of the derivatized species of interest are treated with exoglycosidases. Each individual sample is treated with a single different exoglycosidase. The products of this exoglycosidase treatment are resolved in an electrophoretic medium. The exoglycosidase which acts on the derivatized species of interest is identified. In the case of a typical linear (unbranched) oligosaccharide, only one exoglycosidase will act to cleave a single monosaccharide unit from the non-reducing end of the derivatized species of interest to produce a derivatized species of interest having size $X-1$. The cleavage data is correlated with known exoglycosidase specificities to determine the identity of the monosaccharide cleaved from the non-reducing terminus.

The derivatized species of interest having size $X-1$ is isolated and the complete sequence of monosaccharides in the oligosaccharide of interest is determinded by sequentially repeating the exoglycosidase treatment and electrophoretic analysis steps specified above to determine the monosaccharide unit present at the non-reducing terminus of progressively shorter oligosaccharide units, each progressively shorter oligosaccharide unit differing from its parent by a single monosaccharide unit.

The methods described herein facilitate the separation and monosaccharide sequence determination of microgram quantities of an oligosaccharide of interest, whereas the prior art methods required milligram quantities. Furthermore, the separation methods described herein enable the separation of complex oligolosaccharide mixtures heretofore unresolveable. In addition, the methods described herein do not require special detection systems, but rather employ basic apparatus used routinely in biochemical research.

DETAILED DESCRIPTION OF THE INVENTION

This invention is based on the discovery that neutral or weakly acidic oligosaccharide species can be derivatized to facilitate electrophoretic separation. In one aspect, the methods of this invention pertain to the isolation of an oligosaccharide of interest from a mixture of oligosaccharides. In another aspect, the methods of this invention pertain to the determination of the sequence of monosaccharides in an oligosaccharide of interest.

In another aspect, this invention pertains to methods for determining the monosaccharide sequence of a neutral or weakly acidic oligosaccharide species of interest present as a component of a glycoconjugate. The oligosaccharide components are released from the glycoconjugate by chemical or enzymatic treatment. A labeling compound and a charged group are coupled to the reducing end of the oligosaccharide component to produce a derivatized species of interest. The derivatized species of interest is isolated from the other oligosaccharide components in an electrophoretic medium and its sequence is determined as described above.

The term oligosaccharide, as used herein, is defined as a molecule composed of more than a single saccharide unit where these units are connected through glycosidic linkages. As used within this application, the term oligosaccharide would also include high molecular weight oligomers known as polysaccharides. The only requirement is that the oligosaccharide (or polysaccharide) must either have a reducing end or it must be possible to generate a reducing end by chemical or enzymatic means.

One of the problems associated with the sequencing of oligosaccharides is that typically oligosaccharide preparations contain a mixture of oligosaccharide species of different sizes (polydispersity). In addition, chains having the same monomer number may have different primary structure of sequences (heterogeneity). The fractionation of such mixed populations of oligosaccharide species by gel electrophoresis has been described for acidic oligosaccharide species (i.e. oligosaccharides having a pKa of about 2.5 or less). However, most oligosaccharides are neutral or weakly acidic and do not carry a charge sufficient to facilitate electrophoretic separation.

The methods of this invention, in one aspect, facilitate the isolation of a neutral or weakly acidic oligosaccharide species (i.e. oligosaccharides having a pKa of about 2.5 or greater) by electrophoresis. This is accomplished by first coupling a charged group and a labeling compound to the reducing ends of the oligosaccharide species in the mixture. This step accomplishes two objectives. First, the labeling group attached to the reducing end of the oligosaccharide provides a marker at a specific location in the molecule which can be detected, for example, in an electrophoretic medium. Secondly, the electrical charge of the labeling compound is responsible for the migration of the oligosaccharide species when placed under the influence of an electrical field.

The reducing end can be labeled with any labeling compound including, for example, fluorescent, radioactive or UV-active compounds. The charged group can be added in a single step reaction with the labeling compound as described below, or the labeling compound and the charged group can be added to the reducing end in separate steps. Preferred charged groups include sulfate, phosphate or quatenary ammonium groups.

In a preferred embodiment, the reducing ends of the oligosaccharide species are derivatized by reaction with fluorescent, negatively charged molecules. For example, two such compounds are 7-amino-1,3-naphthalenedisulfonic acid, monopotassium salt and 1-aminopyrene-3,6,8,-trisulfonic acid, trisodium salt. These two compounds derive their negative charge from the sulfate groups, however, other charged groups such as phosphate, quatenary ammonium, etc., can be used. The details of such a derivatization reaction are described in the Exemplification below.

The oligosaccharide mixture bearing the charged labeling group is then resolved into its constituent species by electrophoresis. In a preferred embodiment, the electrophoretic medium is a polyacrylamide gel. The polyacrylamide gel can be of uniform pore size, or a gradient gel can be used. A particularly useful gradient range is from 12% cross-linking at the top, to 22% cross-linking at the bottom, and includes a conventional stacking gel.

An alternative method relies on capillary electrophoresis to resolve an oligosaccharide mixture bearing the charged labeling group into its constituent species. Electrophoresis is done in a narrow bore capillary tube. This tube can be empty as in capillary zone electrophoresis (CZE). In CZE the interaction of the charged oligosaccharide with the internal wall of the capillary under the influence of an electric field results in a separation based primarily on molecular charge. The capillary can be filled, either with a polyacrylamide gel (capillary gel electrophoresis) or with a viscose solution of polyethylene glycol or dextran (capillary dynamic sieving electrophoresis) and a separation based primarily on oligosaccharide size results.

Following electrophoresis, the resolved oligosaccharide species are recovered from the electrophoretic medium. A preferred method for recovering the resolved oligosaccharide species from a gel is by electrotransfer to a charged solid support. Particularly preferred is the semi-dry electrotransfer described in detail in the Exemplification. The electrotransfer of charged molecules, other than oligosaccharides, from a gel to a charged solid support is well known in the art. Examples of appropriate charged solid support materials include nylon membranes, nitrocellulose, etc. The support bound oligosaccharides are released from the support by incubation in an appropriate buffer, desalted, for example, by dialysis and concentrated, for example, by lyophilization. One skilled in the art would know or could devise numerous methods for recovering the resolved oligosaccharide species from the preparative acrylamide gel.

In the case of capillary electrophoresis, resolved oligosaccharide species can be recovered by simply repetitively running them out of the capillary tube into a fraction collector.

Figure 5:
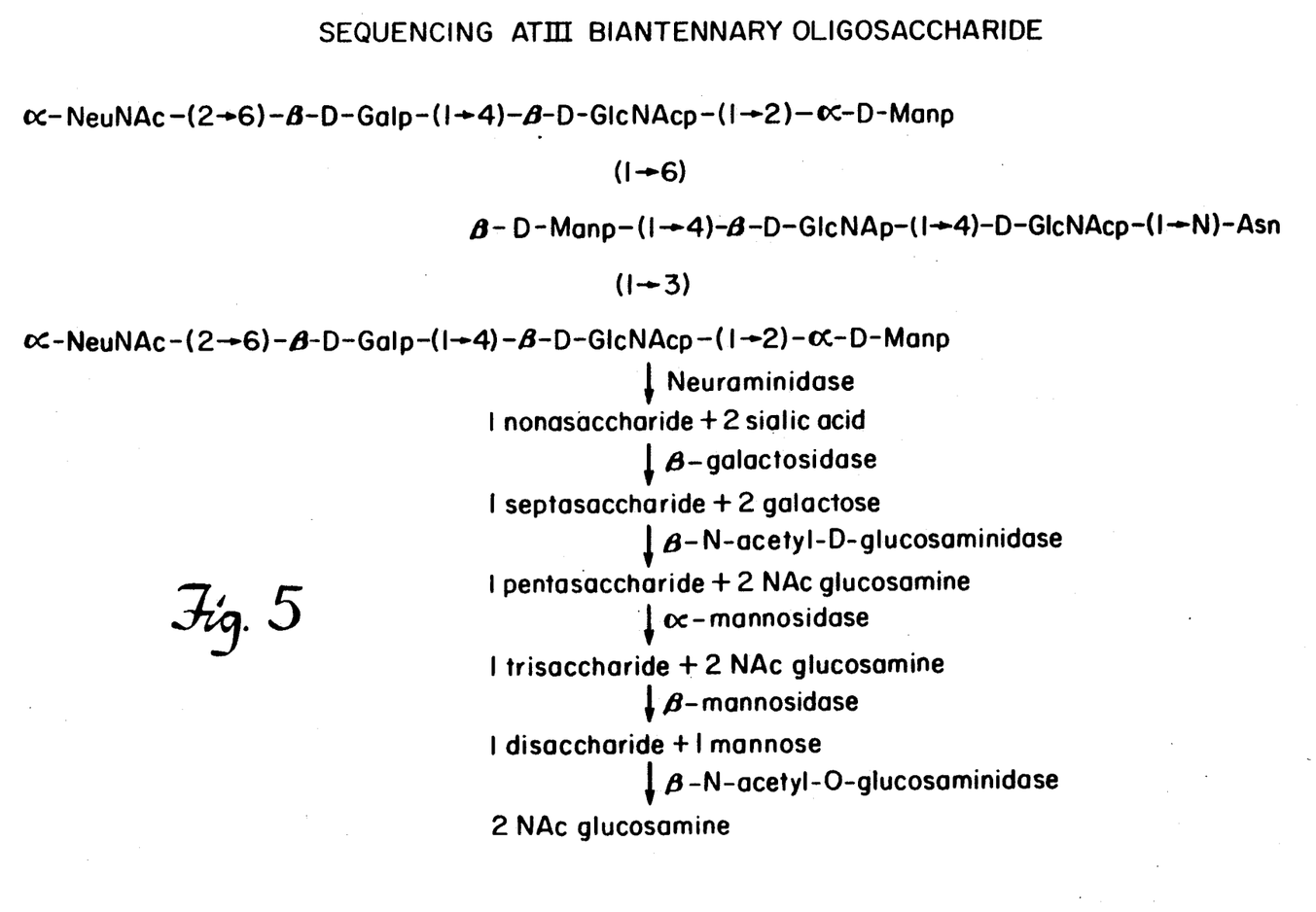
FIG. 5 is a diagram showing a scheme for sequencing a typical bianternnary oligosaccharide species that has been labeled and charged.

The recovered oligosaccharide, having a charged label can be used in several ways. First, the label can be removed by chemical or enzymatic methods. For example, the labeled bianternnary oligosaccharide, shown in FIG. 5, could be treated with hydrazine or with endoglycosidase F(EC3.2.1.96, Genzyme). This affords a pure oligosaccharide for various applications. Second, the recovered labeled oligosaccharide can be used as a substrate for exoglycosidases and would be useful in assessing purity of exoglycosidase preparations. Finally, the labeled oligosaccharide can be sequenced.

In another aspect of the present invention, a method is described for determining the monosaccharide sequence of a neutral or weakly acidic oligosaccharide species of interest having a size X. The variable term X is used herein to denote the number of monosaccharide units in the oligosaccharide of interest. The oligosaccharide species of interest, is derivatized as described above, to couple a labeling compound and a charged group to the reducing end of the oligosaccharide.

To determine the monosaccharide sequence, samples or aliquots of the derivatized oligosaccharide species of interest are treated with exoglycosidases, each sample or aliquot being treated with a single exoglycosidase. Enzymatic hydrolysis can be carried out on very small quantities of the recovered oligosaccharide species. Exoglycosidases are hydrolases which cleave monosaccharide units from the non-reducing terminus of oligosaccharides. Since exoglycosidases cleave only monosaccharide residues that are located at the non-reducing terminus, they are useful tools for sequencing the oligosaccharide chain. In addition, information about the anomeric configuration of glycosidic linkages can be obtained by using the known specificity of glycosidases. A partial list of exoglycosidases known to be useful are presented in Table 1.

osaccharide is revealed by determining which of the tested enzymes resulted in a cleavage of the oligosaccharide (as evidenced by the altered mobility of the labeled fragment in the electrophoretic medium).

Figure 1:
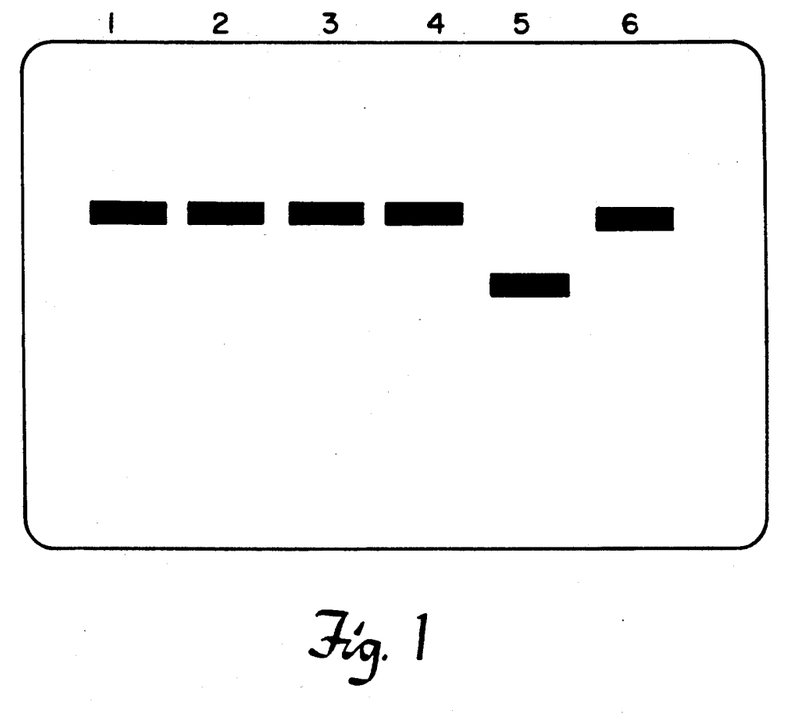
FIG. 1 is a diagram representing an electrophoretic display of the reaction products following exoglycosidase treatment of a labeled nonasaccharide species.
Figure 2:
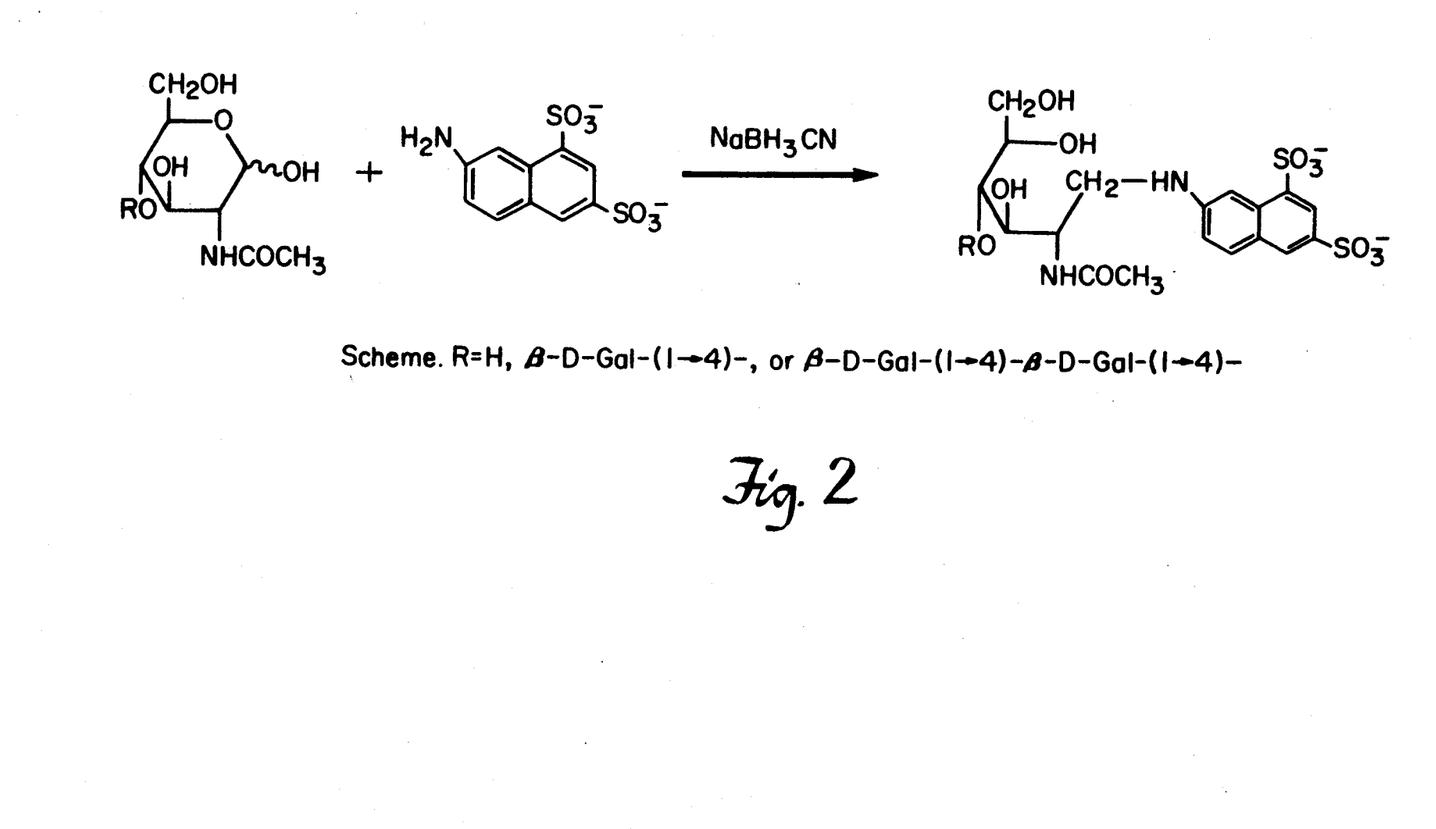
FIG. 2 is a diagram representing a method for labeling an oligosaccharide or polysaccharide with a charged fluorescent tag.
Figure 3A:
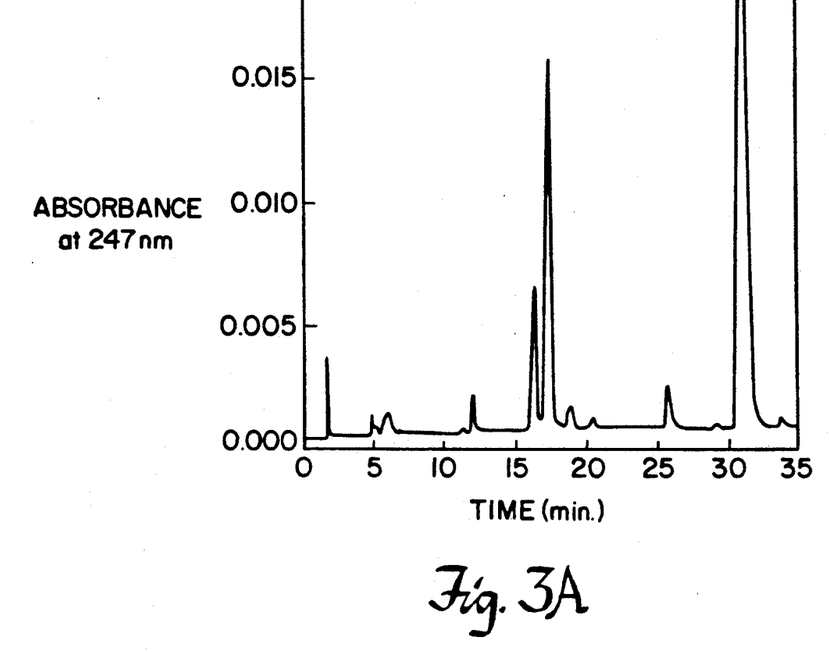
FIG. 3 is a diagram representing a strong anion exchange HPLC analysis of sugar conjugates.
Figure 3B:
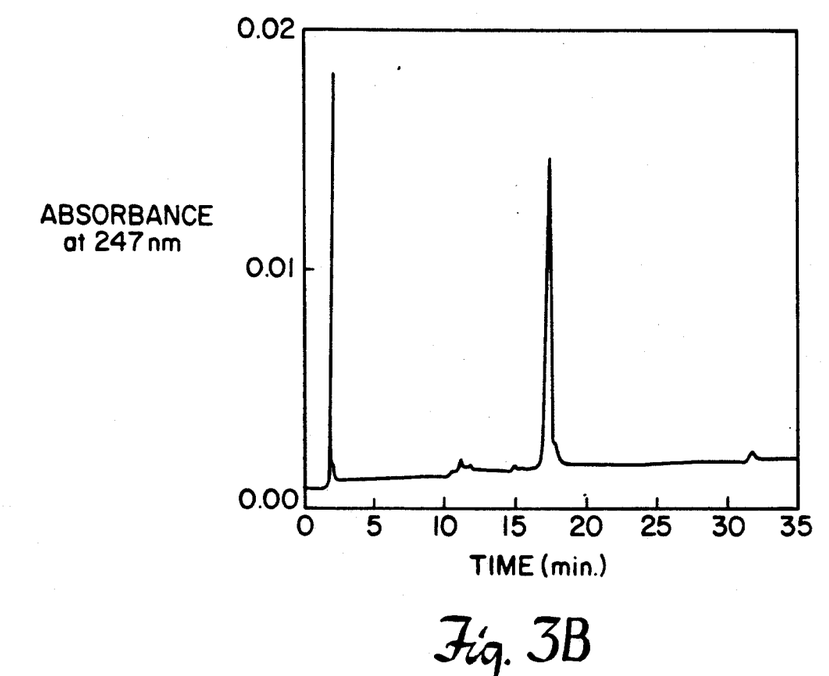
Figure 4:
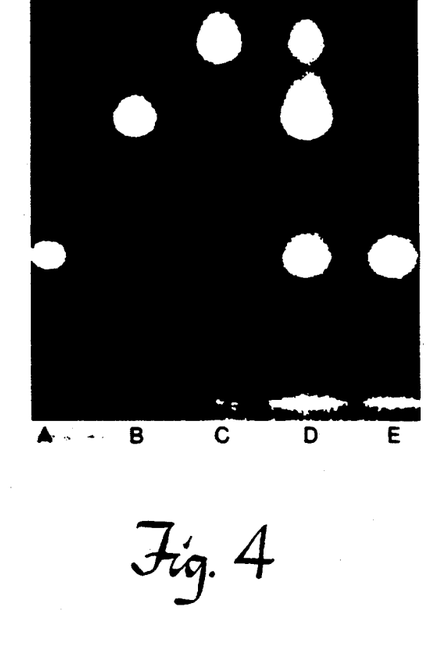
FIG. 4 is a diagram representing sequence analysis of a sugar-AGA conjugate by gradient polyacrylamide gel electrophoresis.

More specifically, for example, FIG. 1 represents the electrophoretic separation of the reaction products from a battery digest of an nonasaccharide (as shown in step 2, FIG. 5) containing the monosaccharides galactose at its two non-reducing ends. Lane 5 represents the reaction mixture containing β-galactosidase which specifically releases β-D-galactose. The released monomers would not be detectable in the gel because they are unlabeled. If it becomes desirable to detect released monosaccharide, labeling with the same tag (or a different tag) containing a charged group, can be performed after its enzymatic release. The labeled oligosaccharide

TABLE 1

| EXOGLYCOSIDASES | | | |
|---|---|---|---|
| Enzyme | Source | Specificity | References |
| α-L-fucosidase (EC 3.2.1.51) | *Charonia lampas* | very broad, all fucosyl linkages | (1, 2) |
| α-D-galactosidase (EC 3.2.1.22) | Coffee bean | very broad aglycone | (3) |
| α-mannosidase (EC 3.2.1.24) | Jack bean | Man-α-(1→2)-Man, Man-α (1→6)-Man with 100%, and Man-α-(1→3)-Man with 7% reaction rate | (4) |
| α-glucosidase (EC 3.2.1.20) | Yeast | α-(1→2), α-(1→3), and α-(1→4) glycopyranosides, whereas α-(1→6) bonds are only attacked slowly | (5) |
| Neuraminidase (EC 3.2.1.18) | *Clostridium perfringens* | NeuAc-α-(2→3)-Gal NeuAc-α-(2→6)-Gal, and NeuAc-α-(2→6)-GalcNAc | (6) |
| β-glucuronidase (EC 3.2.1.31) | *E. coli* K 12 | β-D-glucuronides | (7) |
| β-glucosidase (EC 3.2.1.21) | *Amyodalae dulces* | β-glucosides of phenols, salicyl alcohol, vanilin, 2-cresol and 4-cresol | (8) |
| β-galactosidase (EC 3.2.1.23) | Bovine testes | Gal-β-(1→3)-GlcNAc Gal-β-(1→4)-GlcNAc Gal-β-(1→4)-GalNAc | (9, 10) |
| | *Streptococcus pneumoniae* | Gal-β-(1→4)-GlcNAc No cleavage of Gal-β-(1→3)-GlcNAc or Gal-β-(1→6)-GlcNAc | |
| β-N-acetyl-D-glucosaminidase (EC 3.2.1.30) | Beef kidney | N-acetyl-β-D-glucosaminides, N-acetyl-β-D-galactosamindes | (11) |
| β-N-acetyl galactosaminidase (EC 3.2.1.4) | *Aspergillus niger* | GalNAc-ser link | (12) |

(1) Iijima, Y. and F. Egami, J. Biochem. (Tokyo) 70:75 (1971).
(2) Nishigaki, M. et al., J. Biochem. (Tokyo) 75:509 (1974).
(3) Courtois, J. E. and F. Pertek, Methods Enzymol 8:565 (1966).
(4) Yamashita, K. et al., J Biol. Chem. 255:5635 (1975).
(5) Halvorson, H., Methods Enzymol. 8:559 (1966).
(6) Cassidy, J. T. et al., J Biol. Chem. 240:3501 (1965).
(7) Bergmeyer, H. U. et al., Methods of Enzymatic Analysis. Bergmeyer, H.U., ed., VCH, New York, pp. 246–256.
(8) Conchie, J. et al., Biochem. J. 103:609 (1967).
(9) Uchida, Y. et al., J. Biochem (Tokyo) 80:1573 (1979).
(10) Paulson, J. C. et al., J. Biol. Chem. 253:5617 (1978).
(11) Glasgow, L.R. et al., J. Biol. Chem. 252:8615 (1977).
(12) McDonald, M. J. and O. P. Bahl, Methods Enzymol 28:734 (1972).

The products of the individual exoglycosidase reaction mixtures are then separated by electrophoresis. As discussed above, in connection with the purification of individual species, preferred embodiments include polyacrylamide gradient gel, electrophoresis and capillary electrophoresis. Since the label is located at the reducing end of the oligosaccharide chain, the digestion products are a monosaccharide and a smaller labeled oligosaccharide having size X−1. Because each exoglycosidase specifically recognizes and cleaves only one type of monosaccharide from the non-reducing end of the oligosaccharide chain, the identity of the terminal monosaccharide is revealed by determining which of the tested enzymes resulted in a cleavage of the oligosaccharide (as evidenced by the altered mobility of the labeled fragment in the electrophoretic medium).

represented in lanes 1–4 is not cleaved by the other exoglycosidases and, therefore, its electrophoretic mobility is unchanged. Lane 6 represents a sample of the labeled oligosaccharide which was not treated with an exoglycosidase and which was run on the gel as a mobility standard.

The labeled oligosaccharide contained within the lane of the gel corresponding to the reaction mixture containing the enzyme which recognized and cleaved the terminal monosaccharides (lane 5 in this case) is then recovered from the gel, for example, using semi-dry electrotransfer as described herein. The battery digestion procedure and electrophoretic display is then repeated to determine each of monosaccharides in the chain thereby revealing the sequence of the oligosaccharide species.

The structure of many oligosaccharide species can be deduced with greater certainty by using enzymes having greater specificity. For example, chains with 1→3 linked galactose at their non-reducing end can be distinguished from ones with a 1→6 linked galactose by using galactosidase (EC3.2.1.23, bovine testes) in place of galactosidase (EC3.2.1.23, *E. coli*). Alternatively, endoglycosidases, such as $\beta$-endogalactosidase (*E. freundii*, EC3.2.1.103) can be used in sequencing. Another complicating structural feature is one in which a labeled oligosaccharide contains two (or more) identical sugars at its non-reducing end and where these sugars are linked in the same configuration. As soon as the exoglycosidase removes the non-reducing end sugar, it exposes a new, identical non-reducing end on which it can act. In such cases, sequencing is accomplished by incompletely treating the labeled oligosaccharide with exoglycosidase. Analysis then shows multiple bands corresponding to unreacted starting material, oligosaccharde of size $X-1$, and oligosaccharide of $X-2$. The sequencing of the labeled oligosaccharide, terminating in two $\beta$ (1→4) linked galactose residues, illustrates this approach.

Sequencing branched oligosaccharides follow the same general scheme as used for linear oligosaccharides. In a branched oligosaccharide (in which each branch terminates with a different sugar) when treated with the set of exoglycosidases described in the previous example (FIG. 1), will show two lanes to have a shifted band. Both shifted bands will then be recovered, by electrotransfer, for example, and sequenced individually. This will result in the sequence of each branch.

The discussion above relating to sequencing has been limited to the analysis of a sample containing a single oligosaccharide species. The method of this invention is also useful for determining the monosaccharide sequence of an oligosaccharide sequence of interest contained within a mixture of oligosaccharides. This can be accomplished by essentially by combining the isolation and sequencing methods described above. That is, the oligosaccharide species present in the mixture are derivatized by the addition of a labeling compound and a charged group at the reducing terminus. These derivatized species are next separated in an electrophoretic medium. The derivatized oligosaccharide of interest is recovered from the medium and subjected to exoglycosidase treatment as described above to determine the monomer sequence.

The methods of this invention are also useful for the determination of the sequence of an oligosaccharide species present as a component of a glycoconjugate. Two very important classes of glycoconjugate are the glycolipids and glycoproteins. The core element of a glycoprotein is a protein which has been modified by cellular enzymes by the covalent addition of one or more oligosaccharide moieties to the side chains of particular amino acid residues by a process known as glycosylation. The most common oligosaccharide linkage is to the side chain of the amino acid asparagine; such linkages are referred to as N-linked oligosaccharides. Oligosaccharides are also known to be linked to the OH group on the side chain of serine, threonine, or hydroxylysine residues; these are referred to as O-linked oligosaccharides.

To determine the sequence of an oligosaccharide species which is a component of a glycoprotein, the oligosaccharide species must first be released from the core element of the glycoprotein. Some glycoproteins contain multiple oligosaccharide components. Glycoproteins can be purified using techniques well known to those skilled in the art. In order to release the oligosaccharide species from the protein core, the glycoprotein is treated with a chemical or enzyme capable of breaking the glycosidic bond which links the oligosaccharide species to the protein core.

Hydrazine treatment can be used, for example, to release oligosaccharides from glycoproteins. Hydrazine cleaves the N-glycosidic linkages of N-glycosylpeptides and N-glycosylproteins and liberates the N-deacetylated glycans as their hydrazones.

Treatment with (1:1) mixtures of trifluoroacetic anhydride and trifluroacetic acid at 100° C. for 48 h also results in cleavage of the glycosylamine protein-carbohydrate linkage. Trifluoroacetolysis cleaves peptide bonds by transamidation and replaces the N-acetyl substituents of amino sugars by N-trifluoroacetyl groups.

O-glycosidic linkages between carbohydrate chain and the beta-hydroxyamino acids serine and threonine are easily cleaved using dilute alkali solution (o.0-5–0.1M NaOH or KOH) under mild conditions (4°–45° C. for 0.5–6 d) by a beta-elimination mechanism.

A preferred method for removing oligosaccharide species from a glyconjugate is by treatment with an endoglycosidase. The endoglycosidase specifically cleaves the glycosidic bond which joins the oligosaccharide to the core element. A preferred endoglycosidase is the enzyme glycopeptidase F(EC3.2.2.18) N-glycanase ™, (Genzyme) which removes N-linked oligosaccharides or endo-α-N-acetylgalactosaminidase (O-glycanase ™, Genzyme).

Similar methods can be used to remove oligosaccharides from glycolipids. Chemical methods include treatment of glycolipid with trifluoroacetic acid/trifluoro acetic anhydride, osmium tetroxide/periodic acid, or ozone/sodium hydroxide or sodium carbonate. Enzymatic methods include the use of ceramide glycanase (endoglycoceramidase, Boerhinger Mannheim).

The invention is illustrated further by the following Exemplification.

EXAMPLES

Example 1

Materials and Methods

Chemicals

N-acetyl-D-glucosamine (2-acetamido-2-deoxy-D-glucose), N-acetyl-D-galactosamine (2-actamido-2-deoxy-D-galactose), D (+)-mannose, D (+)-glucose, D (+)-galactose, L (+)-arabinose, N-acetyl-lactosamine (2-acetamido-2-deoxy-4-O-$\beta$-D-galactopyranosyl-D-glucopyranose; $\beta$-D-galactopyranosyl-[1→4]-N-acetyl-D-glucosamine), lacto-N-biose(2-acetamido-2-deoxy-3-O-$\beta$-D-galactopyranosyl-$\beta$-D-glucopyranose; $\beta$-D-galactopyranose-[1→3]-N-acetyl-D-glucosamine), maltose (4-O-α-D-glucopyranosyl-D-glucose), 2-acetamido-2-deoxy-4-O-([4-O-$\beta$-D-galactopyranosyl]-$\beta$-D-galactopyranosyl-D-glucopyranose; $\beta$-D-galactopyran ose-[1→4]-$\beta$-D-galactopyranose-[1→4]-N-acetyl-D-glucosamine, maltoheptose, maltooligosaccharide mixtures ({-$\beta$-D-glucopyranose-[1→4]}$_{4\text{-}10}$), sodium cyanoborohydride, β-galactosidase (from jack beans, *Escherichia coli* and bovine testes) were obtained from Sigma Chemical Co., St. Louis, MO, USA. Monopotassium 7-amino-1,3-naphthalenedisulfonic acid (Amido-G-acid; AGA), and $^2H_2O$ (99.996%) were purchased from Aldrich, Milwaukee, WI, USA. Trisodium 1-aminopyrene-3,6,8-trisulfonic acid (APTS) was purchased from Lamda Probes & Diagnostics, Grottenhof, Austria. Spectrapore dialysis tubing (Mr cut-off 100 and 500) was purchased from Spectrum Medical, Los Angeles, CA, USA. Bio-P2-gel was from Biorad, Richmond, CA, USA. Acrylamide (ultrapure), Tris, alcian blue dye, bromophenol blue dye and ammonium persulfate were obtained from Boehringer Mannheim Biochemicals, Indianapolis, IN, USA. Glycine hydrochloride, disodium EDTA, boric acid, sucrose, N,N-methylene bisacrylamide and N,N,N,N-tetramethylenediamine (TEMED) were from Fisher Chemical Company, Fair Lawn, NJ, USA. Biotrace RP nylon and nitrocellulose membranes were obtained from Gelman Science Inc., Ann Arbor, MI, USA., 3 mm paper, from Whatman, Hillsboro, OR, USA. Bio-P2 gel was purchased from Biorad, Richmond, CA, USA. Sodium 2,2-dimethyl-2-silapentane-5-sulfonate (DSS) was obtained from Merck Sharp & Dohme, Kirkland, Quebec, Canada. All other chemicals were reagent-grade.

Equipment

Strong-anion-exchange high performance liquid chromatography (SAX-HPLC) was performed using two Shimadzu Bio Liquid Chromatograph LC-7A pumps (Kyoto, Japan) with gradient control by digital to analog interface using an Apple IIe microcomputer running Chromatochart software from Interactive Microware Inc., State College, PA, USA. The system was equipped with a fixed-volume loop Rheodyne (Cotai, CA) #7125 injector and 2141 variable wavelength detector from Pharmacia LKB Biotechnology, Inc., Piscataway, NJ, USA. The data was processed using a Shimadzu Chromatopac C-R3A integrating recorder. SAX-HPLC was performed on a Spherisorb (5 μm particle size) column of dimensions 4.6 mm×25 cm, with a 4.6 mm×5 cm guard column from Phase Separations, Norwalk, CT, USA. A 32 cm×16 cm vertical slab gel unit (SE 620), 250 ml SG500 linear gradient maker apparatus and the TE70 semi-dry electrophoretic transfer unit were obtained from Hoefer Scientific Instruments, San Francisco, CA, USA. An electrophoresis power unit model 1420B and trans-blot electro-transfer system were purchased from Biorad, Richmond, CA, USA. Sugar-florescent conjugates were visualized in the ultraviolet light chamber from Ultra-violet Products, Inc., San Gabriel, CA, USA. Freeze-drying was done on a Virtis Freezemobile 6 freeze-drier.

Methods

Preparation of Fluorescence Labeled Standard Sugars by Reductive Amination Method AGA was used after recrystallization from deionized water (The Merck Index, 11th Edition, Merck & Co., Inc., Rahway, NJ, p. 66, (1989)). A standard sugar (3.5 μmol) was dissolved in 720 μl AGA or APTS solution (50 wt %, pH 6.2). After heating at 80° C. for 1 h, 36 μl of reducing agent was added. The reducing agent was prepared by mixing 10 mg of sodium cyanoborohydride, 20 μl AGA solution and 30 μl of water. The mixture was heated and agitated at 100 rpm for 24 h at 65° C. in an incubator shaker. After the reaction was complete, the products were dialyzed overnight at 40° C. against double distilled deionized water in either 100 (for monosaccharides and disaccharides) and 500 (for trisaccharides) Mr cut-off controlled pore dialysis bags. The samples were freeze-dried and reconstituted in 100 μl of distilled water before loading on the preparative gel.

Preparation and Electrophoresis of Gradient Polyacrylamide Gels

Gradient polyacrylamide resolving gel was prepared from two different resolving gel concentrations. The back chamber contained 11.5% (W/V) N,N-bisacrylamide, 0.5% (W/V) N,N-bisacrylamide and 1% (W/V) sucrose in resolving buffer (lower buffer chamber) made from 0.1M boric acid, 0.1M Tris and 0.01M disodium EDTA, pH 8.3 (Rice, K.G. et al., *Biochem. J.* 244:515-522 (1987)). The mixing chamber contained 20% (W/V) of N,N-acrylamide, 2% (W/V) N,N-bisacrylamide and 15% (W/V) of sucrose, pH 8.3, in resolving buffer. Gels were poured vertically between two glass plates (16 cm×32 cm) separated by 1.5 mm spacers. Gradients were poured by adding 35 ml of 12% solution (degassed) to the reservoir (back chamber) and 35 ml of 22% solution (degassed) to the mixing chamber. Ammonium persulfate, 400 μl of 10% solution, was added to the reservoir and 200 μl to the mixing chamber followed by addition of 30 μl of TEMED to both the reservoir and mixing chamber. The solutions were mixed thoroughly. The acrylamide solution in the mixing chamber was continuously mixed using a magnetic stirrer. The valve between the reservoir and the mixing chamber was opened. Polyacrylamide solution from the mixing chamber passed by gravity into two channels leading to the top of the glass plates forming a linear gradient from bottom to top. The unpolymerized solution was overlaid with water. Polymerization occurred from top to bottom. After polymerization had completed, the water layer was removed. Ten ml of stacking gel made from 4.75% (W/V) N,N-acrylamide and 0.25% (W/V) N,N-bisacrylamide in resolving buffer but adjusted to pH 6.3 with hydrochloric acid was mixed. Ammonium persulfate, 135 μl of 10%, and 10 μl of TEMED was added to the top of the resolving gel. A desired comb (well former) was inserted. After polymerization, the comb was removed and the walls were washed with water and upper buffer chamber was filled with a buffer made from 1.25M glycine and 0.2M Tris pH 8.3. Samples combined with an equal volume of 50% sucrose solution containing trace quantities of phenol red and bromophenol blue were loaded carefully to the bottom corner of each well. Electrophoresis was performed for 18 hours at 400 volts with cooling using circulating tap water. The gel was removed from the glass plate and, if necessary, stained with alcian blue 0.5% (W/V) in 2% V/V aqueous acetic acid for 30 minutes. Destaining was carried out using several 200 ml volumes of distilled water.

Semi-Dry Electro-Transfer

The resolving gel was visualized using a ultraviolet light and the desired fluorescent band was located. The band was removed from the gel by carefully cutting the gel. This slice was then soaked in transfer buffer consisting of Tris base (5.82 g), glycine hydrochloride (4.35 g) and methanol (200 ml) made up in 1 l with double distilled deionized water. Several layers of blotting paper and positively charged transfer nylon membranes were cut to the same size as the gel and soaked in transfer buffer. Two pieces of transfer buffer-saturated blotting papers (3 mm) were placed on the top of the Mylar Mask, centering them over the opening. Multiple layers of saturated nylon membranes (depending on the quantity of sample on the gel) were placed on the top of the blotting papers. The soaked gel was placed directly on the nylon membranes followed by 3 layers of blotting papers, thus constructing a transfer sandwich. The cover of the semi-dry transfer unit was placed over the transfer sandwich and electro-transfer was performed at 7-10 V for 1 hour. Completion of the transfer process was ensured by examining the gel under unltraviolet light and making sure that no material was left behind. The nylon membranes were removed and the sample was recovered as described below.

Elution and Recovery of Membrane-Bound Sugar-Fluorescent Conjugates

Bands on the nylon membrane were located and visualized using ultraviolet light at 366 nm. Nylon membranes were cut into small pieces and immersed in test tubes containing 3 ml of 2.0M sodium chloride and placed on a shaker for several hours at room temperature. The salt solution containing recovered materials were dialyzed against double distilled deionized water. In the case of the trisaccharide derivative, desalting was performed on a 2.5 cm×75 cm Bio-P2 gel low pressure column. The salt-free sample solution was concentrated by freeze drying.

Spectroscopic Methods

The ultraviolet spectra of the AGA and purified sugar-AGA conjugates were obtained with a Shimadzu UV-160 spectrophotometer (Kyoto, Japan). The samples were prepared in double distilled deionized water by serial dilution. All spectroscopic measurements were performed in 1.0 ml quartz cuvette at room temperature. Fluorescence characteristics of AGA and purified sugar-AGA derivatives that include excitation and emission spectra were recorded in a standard 3.0 ml quartz cuvette at room temperature by using Shimadzu RF-540 spectrofluorophotometer interfaced with a Shimadzu Data Recorder DR-3 (Kyoto, Japan). The excitation and emission slits were 10 nm. The samples were prepared by serial dilution in double distilled deionized water. One and two-dimensional NMR spectroscopy was performed on a Bruker WM-360 or MSL-300 spectrometer operating under ASPECT 2000 or 3000 control. Samples were prepared in $^2H_2O$ (>99.996%) containing DSS as the internal standard at room temperature. Two-dimensional COSY-45 experiment was run using standard Bruker software. Mass spectrometry was performed on a VG ZAB-HF spectrometer in the fast atom bombardment (FAB) ionization mode. Negative-ion FAB spectra were obtained using triethanolamine as the matrix (Mallis, L.M. et al., *Anal. Chem.* 61:1453-1458 (1989)).

SAX-HPLC Analysis

SAX-HPLC was performed to monitor the derivatization reaction and to determine the purity of sugar-fluorescent conjugates obtained using preparative gradient gel electrophoresis. The column was eluted with a linear gradient [concentration (y, in M) at any time (X, in s) +0.0002 X=0.2] of sodium chloride at pH 3.5 and a flow rate of 1.5 ml/min (Linhardt, R.J. et al., *Biochem. J.* 254:781-787 (1988)). The elution profile was monitored by absorbance at 247 nm at 0.02 absorbance units full scale (AUFS).

Enzymatic Digestions

Approximately 5 μg of β-D-galactopyranose-[1→4]-β-D-galactopyranose-[1→4]-N-acetyl-D-glucosamine-AGA derivative was treated overnight with 0.1 unit of jack bean β-galactosidase at 25° C. in a 100 μl of 0.2M citrate buffer, pH 3.5. The same amount of β-D-galactopyranose-[1→4]-β-D-galactopyranose-[1→4]-N-acetyl-D-glucosa mine-AGA derivative was also treated overnight with 100 units of *Escherichia coli* β-galactosidase at 37° C. in a 100 μl of 0.1M phosphate buffer, pH 7.3. Both enzymatic reactions were performed with agitation in an incubator shaker at 100 rpm.

Results

The molar ratio of sugar, AGA and sodium cyanoborohydride was optimized by using N-acetylglucosamine and N-acetylactosamine as reference sugars. The reaction was monitored by running each sample on the gradient PAGE and visualizing the products in the ultraviolet light chamber at 366 nm. To drive the reaction to completion, a large excess of ACA and longer reaction times were applied to the larger oligosaccharides. Six monosaccharides (N-acetyl-D-glucosamine, N-acetyl-D-galactosamine, D (+)-mannose, D (+)-glucose, D (+)-galactose, and L (+)-arabinose), three disaccharides (N-acetylactosamine, lacto-N-biose, and maltose), one trisaccharide (2-acetamido-2-deoxy-4-O-{[4-O-β-D-galactopyranosyl]-β-D-galactopyranosyl)-D-glucopyranose; β-D-galactopyranose-[1→4]-[1→4]-N-acetyl-D-glucosamine), maltoheptose, and maltooligosaccharide mixtures were successfully labeled with the AGA reagents.

Gradient polyacrylamide gel electrophoresis has been used extensively in the present work due to its effectiveness and simplicity in resolving, separating and identifying the desired products. The PAGE system acts as a purifying tool for the crude reaction mixture as well as a visualizing system for the resolved fluorescent bands. Previous workers (Linhardt, R.J. et al., *Biochem. J.* 254:781-787 (1988)) have used multiple separation steps including extraction, high pressure liquid chromatography and thin layer chromatography to obtain the final products. The method described here replaces these time consuming, labor intensive procedures with a single electrophoresis step. Crude products are loaded directly on gradient gel and fractionated by electrophoresis. The sugar-fluorescent conjugates appear as well resolved bands under ultraviolet light. The desired product can be isolated by electro-transfer from the gel onto a positively charged nylon membrane. Analysis by SAX-HPLC shows the difference in purity between the crude and the isolated products. Electrophoresis is usually carried out for 18 hours and the gel can be visualized instantly, without any further development, under ultraviolet light. Electro-transfer using the semi-dry procedure is a 15-minute technique capable of quantitatively recovering purified sugar-fluorescent conjugate. Preparative gradient PAGE on 1.5 mm gels can be used to fractionate 100 mg of sample while 3 mm thick gels permit the loading of up to 1 g of sugar-fluorescent conjugate. Analytical gradient PAGE is also valuable for analyzing nanogram quantities of sugar-fluorescent conjugate.

The structures of sugar-AGA conjugates were established using spectroscopic and enzymatic methods. Ultraviolet absorption spectra of the AGA and the sugar-AGA conjugates were compared. Ultraviolet spectrum of AGA exhibits maximum at 247 nm ($\epsilon = 0.31 \times 10^2 M^{-1} cm^{-1}$). The trisaccharide-AGA conjugate, the disaccharide-AGA conjugate (N-acetyllactosamine-AGA) and the monosaccharide-AGA conjugate (N-acetylglucosamine-AGA) all shows a 256 nm maxima.

The fluorescence spectra of sugar-AGA conjugates were also obtained. AGA itself shows the emission maxima at 447 nm and a excitation maxima at 343 nm. Sugar-AGA conjugates (mono-, di-, and trisaccharides), show an emission maxima is at 452 nm and an excitation maxima at 365 nm. Excitation and emission spectra of all of the sugar-AGA conjugates are very similar. Sugar-AGA conjugates can be detected using a fluorimeter at femtomolar concentrations. But, in the ultraviolet light chamber at 366 nm picomole amounts of sugar-AGA conjugate are easily detected by the human eye.

Purity of the sugar-AGA conjugates obtained using preparative gradient PAGE was evaluated by SAX-HPLC. AGA and sugar-AGA conjugates could be separated by SAX-HPLC. AGA-N-acetylglucosamine, AGA-N-acetyllactosamine, and $\beta$-D-galactopyranose-[1→4]-$\beta$-D-galactopyranose-[1→4]-N-acetyl-D-glucosamine, purified by gradient PAGE, were separated under sodium chloride linear gradient conditions. SAX-HPLC of crude reaction mixtures (without any purification) resulted in two major peaks corresponding to AGA and sugar-AGA conjugate.

The negative-ion FAB-MS spectrum of the trisaccharide-AGA derivative showed a molecular ion at m/z 853 [M-Na]$^-$ consistent with its molecular weight of 876. The ion at m/z 912 corresponds to addition of one molecule of NaCl to the molecular ion at m/z 853. The fragment ion at m/z 692 is the result of the loss of one galactose residue at the non-reducing end. The ion corresponding to the loss of second galactose residue was not observed in the spectrum. A detailed NMR study was also undertaken to unambiguously characterize the sugar-AGA conjugate, particularly to determine the structure of the linking chain. Earlier studies on the reductive amination reported that monosaccharide or oligosaccharides containing N-acetylglucosamine at the reducing end give rise to low yields (Rosenfelder, G. et al., *Anal. Biochem.* 147:156–165 (1985)). The exact structure of linking sugar chain in the products had not been unambiguously established.

N-acetylglucosamine-AGA and the trisaccharide-AGA conjugate, purified by preparative PAGE method, were examined by $^1$H NMR spectroscopy. In both cases, the absence of anomeric proton signal of N-acetylglucosamine residue and a slight upfield shift of H-6 and H-8 protons (compared to AGA) support their structure. Two-dimensional COSY spectrum of N-acetylglucosamine-AGA derivative fully established its structure.

Sugar-AGA conjugates can be used for sequencing oligosaccharides by following exoglycosidase treatment on the gel electrophoresis. For this sequencing strategy to be successful, the sugar-AGA conjugates must retain their sensitivity to exoglycosidases. To test this, trisaccharide-AGA conjugate was treated with three different $\beta$-galactosidases (jack bean, *E. coli* and bovine testes). Treatment with jack bean and *E. coli* $\beta$-galactosidase resulted in the disappearance of the trisaccharide-AGA conjugate band and the appearance of a lower molecular weight band corresponding to the monosaccharide-AGA conjugate. This indicated that the carbohydrate portion of trisaccharide-AGA derivative retains its sensitivity to $\beta$-galactosidase (an exoglycosidase). Therefore, sugar-AGA conjugates can be used for sequencing analysis by exoglycosidase digestion. Because $\beta$-galactosidase acts at a site near to the derivatizing compound, it is reasonable to expect the derivatized oligosaccharides (e.g., glycoprotein released oligosaccharides, proteoglycans) would retain their sensitivity to other exoglycosidases (e.g., neuraminidase, mannosidase, N-acetylgalctosaminidase) which act at site quite removed from the derivatizing compound. Partial digestion using $\beta$-galactosidase resulted resulted in three bands corresponding to trisaccharide-AGA starting material a disaccharide-ACA conjugate and a monosaccharide-AGA conjugate. This result gives the sequence of the trisaccharide starting material and suggests that it is possible to use their approach to sequence more complex oligosaccharides. The strategy involves: 1) release of oligosaccharides from glycoproteins using an endoglycosidase, such as N-glycanase; 2) conjugation of the released oligosaccharides to AGA; 3) fractionation and purification of each oligosaccharide-AGA conjugate; 4) sequential treatment of each purified oligosaccharide-AGA conjugate with specific exoglycosidases; and 5) analysis by analytical PAGE and reading of the sequence from the observed banding pattern.

Example 2

Sequencing Lacto-N-tetraose

AGA was coupled to the reducing end of lacto-N-tetraose (Gal($\beta$ 1→3)GlcNAc($\beta$ 1→3)Gal($\beta$ 1→4)Glc) (purchased from Sigma Chemical) using the conditions described in Example 1. The lacto-N-tetraose derivative thus prepared was purified by gel electrophoresis and recovered by electrotransfer, as described in Example 1. Freeze-dried, desalted AGA derivative of lacto-N-tetraose (0.5 $\mu$g) was analyzed by gel electrophoresis: 1) directly with no enzymatic treatment; 2) following 12 h treatment with 100 munit $\beta$-galactosidase (*A. Niger*); 3) following treatment with $\beta$-galactosidase (as in 2), thermal inactivation of $\beta$-galactosidase (100° C., 2 min), and 12 h treatment with 10 munit N-acetylglucosaminidase (jack bean); and 4) following treatment with $\beta$-galactosidase, thermal inactivation, treatment with N-acetyl glucosaminidase (as in 3), thermal inactivation of N-acetylglucosaminidase (100° C., 2 min), and treatment with $\beta$-galactosidase (*A. niger*). Individual lanes showed bands corresponding to labeled tetrasaccharide, labeled trisaccharide, labeled disaccharide and labeled monosaccharide. From the known specificity of the enzymes, the sequence for lacto-N-tetraose could be established.

Example 3

Analysis of Oligosaccharides Having a Charged Label Using Capillary Zone Electrophoresis A Capillary Electrophoresis System I (Dionex), equipped with an unfilled capillary (CZE) (65 cm, 75 $\mu$m ID, 375 $\mu$m OD) and using fluorescence detection was used to analyze the monosaccharide-AGA derivative, the disaccharide-AGA derivative and the trisaccharide-AGA derivative described in Example 1. Gravity injection was used to apply 10 nl of sample (10 $\mu$g/$\mu$l) a voltage of 17 kV with 17 $\mu$Amp current was applied using negative polarity. The buffer system used was 20 mM citric acid, pH 2.0. Peaks corresponding to each of the AGA derivatives were detected. This experiment demonstrates that it is also possible to use capillary electrophoresis to sequence oligosaccharides. Capillary electrophoresis has the advantage of permitting easy automation of this sequencing approach.

Equivalents

Those skilled in the art will know, or be able to ascertain using no more than routine experimentation, many equivalents to the specific embodiments of the invention described herein. These and other equivalents are intended to be encompassed by the following claims.

We claim:

1. A method for determining the monosaccharide sequence of a neutral or weakly acidic oligosaccharide species of interest, comprising:
    a) coupling a labeling compound to the reducing end of the species of interest, the labeling compound bearing a charged group selected from the group consisting of sulfate, sulfonate, phosphate or quatenary ammonium groups to produce a charged oligosaccharide species of interest having size X, wherein X is the number of monosaccharide units in the species of interest;
    b) treating individual samples of the charged oligosaccharide species of interest with exoglycosidases, each sample of the derivatized species of interest being treated with a single exoglycosidase;
    c) resolving the reaction products of step b) in an electrophoretic medium to identify the exoglycosidase which cleaves a single monosaccharide unit from the non-reducing end of the charged oligosaccharide species of interest to produce a charged oligosaccharide species of interest having size X−1;
    d) correlating cleavage data with known exoglycosidase specificities to determine the identity of the monosaccharide cleaved from the non-reducing terminus;
    e) isolating the charged oligosaccharide species of interest having size X−1; and
    f) determining the complete sequence of monosaccharides in the charged oligosaccharide species of interest by sequentially repeating steps b)–e) to determine the monosaccharide unit present at the non-reducing terminus of progressively shorter oligosaccharide units, each progressively shorter oligosaccharide unit differing from its parent by a single monosaccharide unit.

2. A method of claim 1 wherein the labeling compound is selected from the group consisting of the monopotassium salt of 7-amino-1,3-naphthalenedisulfonic acid or the trisodium salt of 1-aminopyrene-3,6,8-trisulfonic acid.

3. A method of claim 2 wherein the electrophoretic medium is an acrylamide gel.

4. A method of claim 2 wherein the electrophoretic medium is a capillary electrophoretic medium.

5. A method for determining the monosaccharide sequence of a neutral or weakly acidic oligosaccharide species of interest, the species of interest being a component of a glycoconjugate, comprising:
    a) releasing oligosaccharide components from the glycoconjugate by chemical or enzymatic treatment;
    b) coupling a labeling compound to the reducing end of the oligosaccharide components, the labeling compound bearing a charged group selected from the group consisting of sulfate, sulfonate, phosphate or quatenary ammonium groups to produce a charged oligosaccharide species of interest;
    c) separating the oligosaccharide components in an electrophoretic medium;
    d) recovering the charged oligosaccharide species of interest from the electrophoretic medium;
    e) treating individual samples of the charged oligosaccharide species of interest with exoglycosidases, each sample of the charged oligosaccharide species of interest being treated with a single exoglycosidase;
    f) separating the reaction products of step e) in an electrophoretic medium to identify the exoglycosidase which cleaves a single monosaccharide unit from the non-reducing end of the charged oligosaccharide species of interest to produce a charged oligosaccharide species of interest having size X−1;
    g) correlating cleavage data with known exoglycosidase specificities to determine the identity of the monosaccharide cleaved from the non-reducing terminus;
    h) isolating the charged oligosaccharide species of interest having size X−1; and
    i) determining the complete sequence of monosaccharides in the species of interest by sequentially repeating steps e)–h) to determine the monosaccharide unit present at the non-reducing terminus of progressively shorter oligosaccharide units, each progressively shorter oligosaccharide unit differing from its parent by a single monosaccharide unit.

6. A method of claim 5 wherein the glycoconjugate is selected from the group consisting of glycolipids or glycoproteins.

7. A method of claim 6 wherein the enzymatic treatment comprises contacting the glycoconjugate with an endoglycosidase.

8. A method of claim 7 wherein the endoglycosidase is N-glycanase.

9. A method of claim 5 wherein the labeling compound is selected from the group consisting of the monopotassium salt of 7-amino-1,3-naphthalenedisulfonic acid or the trisodium salt of 1-aminopyrene-3,6,8-trisulfonic acid.

10. A method of claim 9 wherein the electrophoretic medium is a gradient acrylamide gel.

11. A method of claim 9 wherein the electrophoretic medium is a capillary electrophoretic medium.

12. A method of claim 9 wherein the resolved oligosaccharide species are recovered from the electrophoretic medium by electrotransfer to a charged solid support.

13. A method of claim 12 wherein the electrotransfer method is a semi-dry electrotransfer.

14. A method for determining the monosaccharide sequence of a neutral or weakly acidic oligosaccharide species of interest, the oligosaccharide species of interest contained in a mixture of oligosaccharides, comprising:
    a) coupling a labeling compound to the reducing end of the oligosaccharide components in the mixture, the labeling compound bearing a charged group selected from the group consisting of sulfate, sulfonate, phosphate or quatenary ammonium groups to produce a charged oligosaccharide species of interest;

b) separating the charged oligosaccharide components in an electrophoretic medium;

c) recovering the charged oligosaccharide species of interest from the electrophoretic medium;

d) treating individual samples of the charged oligosaccharide species of interest with exoglycosidases, each sample of the charged oligosaccharide species of interest being treated with a single exoglycosidase;

e) separating the reaction products of step d) in an electrophoretic medium to identify the exoglycosidase which cleaves a single monosaccharide unit from the non-reducing end of the charged oligosaccharide species of interest to produce a derivatized species of interest having size $X-1$;

f) correlating cleavage data with known exoglycosidase specificities to determine the identity of the monosaccharide cleaved from the non-reducing terminus;

g) isolating the charged oligosaccharide species of interest having size $X-1$; and h) determining the complete sequence of monosaccharides in the charged oligosaccharide species of interest by sequentially repeating steps d)-g) to determine the monosaccharide unit present at the non-reducing terminus of progressively shorter oligosaccharide units, each progressively shorter oligosaccharide unit differing from its parent by a single monosaccharide unit.

15. A method of claim 14 wherein the labeling compound is selected from the group consisting of the monopotassium salt of 7-amino-1,3-naphthalenedisulfonic acid or the trisodium salt of 1-aminopyrene-3,6,8-trisulfonic acid.

16. A method of claim 14 wherein the electrophoretic medium is an acrylamide gel.

17. A method of claim 14 wherein the electrophoretic medium is a capillary electrophoretic medium.

18. An oligosaccharide having attached, at its reducing end, a labeling compound bearing a charged group selected from the group consisting of sulfate, sulfonate, phosphate or quatenary ammonium groups.

19. An oligosaccharide of claim 18 wherein the labeling compound is selected from the group consisting of the monopotassium salt of 7-amino-1,3-naphthalenedisulfonic acid or the trisodium salt of 1-aminopyrene-3,6,8-trisulfonic acid.

* * * * *